United States Patent [19]

Buxbaum

[11] 4,289,896
[45] Sep. 15, 1981

[54] TRANSESTERIFICATION PROCESS

[75] Inventor: Lothar Buxbaum, Lindenfels, Fed. Rep. of Germany

[73] Assignee: Ciba-Geigy Corporation, Ardsley, N.Y.

[21] Appl. No.: 75,789

[22] Filed: Sep. 17, 1979

[30] Foreign Application Priority Data

Sep. 29, 1978 [CH] Switzerland .................. 10198/78

[51] Int. Cl.$^3$ ............................................ C07C 67/02
[52] U.S. Cl. ................................ 560/92; 260/410.5; 260/410.6; 544/215; 546/198; 546/341; 548/312; 560/1; 560/11; 560/80; 560/84; 560/85; 560/100; 560/105; 560/112; 560/118; 560/122; 560/123; 560/127; 560/234
[58] Field of Search ............... 560/1, 92, 100, 234, 560/11, 80, 84, 112, 118, 122, 123, 127; 260/410.5, 410.6; 544/215; 546/198, 341; 548/312

[56] References Cited

U.S. PATENT DOCUMENTS

| | | | |
|---|---|---|---|
| 2,776,985 | 1/1957 | McKinnis | 560/98 |
| 3,057,908 | 10/1962 | Gruschke | 560/92 |
| 3,098,093 | 7/1963 | Hagemeyer | 560/234 |
| 3,226,360 | 12/1965 | Browne | 560/92 |
| 3,489,722 | 1/1970 | Kotani | 560/92 |
| 3,697,520 | 10/1972 | Winter . | |
| 4,002,600 | 1/1977 | Habermeier . | |
| 4,034,019 | 7/1977 | Habermeier . | |

FOREIGN PATENT DOCUMENTS

| | | | |
|---|---|---|---|
| 573956 | 4/1959 | Canada | 560/234 |
| 45-36734 | 7/1970 | Japan | 560/92 |

OTHER PUBLICATIONS

Groggins, "Unit Processes in Organic Chemistry", 4th Ed., pp. 616–620 (1952).

Primary Examiner—Natalie Trousof
Assistant Examiner—Michael Shippen
Attorney, Agent, or Firm—Luther A. R. Hall

[57] ABSTRACT

Phosphonic acids are suitable catalysts for the transesterification of alkyl esters of carboxylic acids with aliphatic or cycloaliphatic diols containing more than 3 carbon atoms.

12 Claims, No Drawings

TRANSESTERIFICATION PROCESS

The present invention relates to a transesterification process which is carried out in the presence of phosphonic acids as catalysts. The production of polyesters by the melt condensation process is usually carried out in two steps. In a first step, a dicarboxylic acid alkyl ester is transesterified with a diol and the transesterification product is subsequently subjected to a polycondensation in the melt phase until the desired viscosity is attained.

Catalysts are normally employed for both process steps, as the reaction rate is uneconomically slow. It is also known that the quality of the polycondensate can depend decisively on the choice of transesterification catalyst. In addition to an undesirable colour, the resistance of the polyester melt to heat and oxidation is often diminished, in which case it is necessary to add stabilisers in order to counteract the degradation and to obtain polyesters having good physical and mechanical properties.

Numerous transesterification catalysts have already been proposed, e.g. metals, metal alloys, metal compounds and acids. The drawback of solid insoluble catalysts is that they can only be employed in very fine powder form. For this reasin, soluble catalysts, among which are e.g. acids such as phosphoric acid or sulfonic acids, are usually employed in the reaction mixture. Phosphoric acid, however, can be incorporated in the polyester in the form of tribasic acid accompanied by crosslinking reactions, while sulfonic acids tend to cause discolourations on account of the action of air when the polyester is stored. It must also be mentioned that, depending on the composition of the starting materials, the activity of the catalysts can differ widely.

The present invention has for its object to provide a group of catalysts for the transesterification process which, when sufficiently active and especially when using diols containing more than 3 carbon atoms, yield polycondensates of good colour and colour resistance. In addition, these catalysts will simultaneously protect the polyester melt effectively from degradation caused by heat and oxidation during manufacture and result in stable polycondensates being obtained.

Accordingly, the invention provides a process for the transesterification of alkyl esters of mono- and polycarboxylic acids with aliphatic or cycloaliphatic diols containing at least 3 carbon atoms in the molecule, in the presence of an acid catalyst, which comprises carrying out the transesterification in the presence of catalytically effective amounts of one more phosphonic acids of the formula

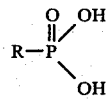

wherein R represents a hydrocarbon radical of aliphatic or aromatic character.

The phosphonic acids are preferably added in amounts of 0.1 to 5% by weight, in particular 0.5 to 2% by weight, based on the amount of the reactants. The hydrocarbon radical R can contain 1 to 20, preferably 1 to 10, carbon atoms.

The hydrocarbon radical R can be linear or branched alkyl, or cycloalkyl, aryl or aralkyl, each of which is unsubstituted or substituted by alkyl of preferably 1 to 12, preferably 1 to 4, carbon atoms.

Examples are: methyl, ethyl, propyl, butyl, isobutyl, pentyl, tert-pentyl, hexyl, heptyl, octyl, nonyl, decyl, dodecyl, tetradecyl, octadecyl, eicosyl, cyclopentyl, cyclohexyl, phenyl, methylphenyl, dimethylphenyl, butylphenyl, benzyl, methylbenzyl or phenylethyl.

The hydrocarbon radical R is in particular an alkyl radical which preferably contains 1 to 10, in particular 1 to 4, carbon atoms, as well as cyclohexyl, phenyl or benzyl.

The transesterification process of the invention is suitable for the alkyl esters of mono- and polycarboxylic acids. Preferred polycarboxylic acids are tricarboxylic acids and, in particular, the dicarboxylic acids employed for the production of polyesters.

The alkyl esters of carboxylic acids are preferably those containing 1 to 10, in particular 1 to 4, carbon atoms in the alkoxy moiety. Particularly suitable alkyl esters are methyl esters, as the readily volatile alcohols can be more easily distilled off from the reaction mixture.

The carboxylic acids can be of aliphatic, cycloaliphatic, heterocyclic or aromatic character. They contain 1 to 40, preferably 1 to 20, carbon atoms.

Suitable monocarboxylic acids are e.g. those containing 1 to 20 carbon atoms, for example aliphatic and cycloaliphatic carboxylic acids, such as formic acid, acetic acid, propionic acid, cyclohexanecarboxylic acid, benzoic acid, naphthalenecarboxylic acid, phenylacetic acid and pyridinecarboxylic acid.

Suitable aliphatic dicarboxylic acids are those containing 2 to 40 carbon atoms, e.g. oxalic acid, malonic acid, dimethylmalonic acid, succinic acid, pimelic acid, adipic acid, trimethyladipic acid, sebacic acid, azelaic acid, and dimeric acids (dimerisation products of unsaturated aliphatic carboxylic acids, such as oleic acid), alkylated malonic and succinic acids, such as octadecylsuccinic acid.

Examples of suitable cycloaliphatic dicarboxylic acids are: 1,3-cyclobutanedicarboxylic acid, 1,3-cyclopentanedicarboxylic acid, 1,3- and 1,4-cyclohexanedicarboxylic acid, 1,3- and 1,4-dicarboxylmethylcyclohexane, 4,4'-dicyclohexyldicarboxylic acid.

Examples of suitable aromatic dicarboxylic acids are: in particular terephthalic acid, isophthalic acid, o-phthalic acid, and 1,3- 1,4- 2,6- or 2,7-naphthalenedicarboxylic acid, 4,4'-diphenyldicarboxylic acid, 4,4'-diphenylsulfone-dicarboxylic acid, 1,1,3-trimethyl-5-carboxyl-3-(p-carboxylphenyl)-indane, 4,4'-diphenyl ether dicarboxylic acid, bis-p-(carboxylphenyl)-methane.

Further suitable dicarboxylic acids are those which contain —CO—NH— groups. They are described e.g. in German Offenlegungsschrift No. 2 414 349. Dicarboxylic acids which contain N-heterocyclic rings are also suitable, for example those which are derived from carboxylalkylated, carboxylphenylated or carboxylbenzylated monoamino-s-triazinedicarboxylic acids (cf. German Offenlegungsschriften Nos. 2 121 184 and 2 533 675), mono- or bishydantoins, unsubstituted or halogenated benzimidazolones, or parabanic acid. The carboxylalkyl group can contain 3 to 20 carbon atoms.

Suitable aliphatic diols for the transesterification are the linear and branched aliphatic glycols, in particular those containing 3 to 10, especially 3 to 6, carbon atoms in the molecule, for example: 1,2- or 1,3-propylene glycol, 1,2-, 1,3-, 2,3- or 1,4-butanediol, pentyl glycol, neopentyl glycol, 1,6-hexanediol, 1,12-dodecanediol. A suitable cycloaliphatic diol is e.g. 1,4-dihydroxycyclohexane.

Further suitable aliphatic diols are e.g. 1,4-dihydroxymethylcyclohexane, aromatic-aliphatic diols, such as p-xylylene glycol or 2,5-dichloro-p-xylylene glycol, 2,2-($\beta$-hydroxyethoxyphenyl)-propane, and polyalkylene glycols, such as diethylene glycol, triethylene glycol or polyethylene glycol. The alkylenediols are preferably linear.

The process of the present invention is carried out batchwise or continuously in apparatus suitable for the purpose and in known manner. A reaction vessel is charged with the reactants and the catalyst and then heated, preferably to 180°–280° C., most preferably to 200°–260° C. The alkanol formed is distilled off during the reaction. A small excess of the diol can also be employed in this reaction.

The process of the invention yields transesterification mixtures which do not contain metal catalysts and are virtually colourless. It is surprising that the group of catalysts employed is almost inactive when ethylene glycol is used as diol. An optimum catalytic activity is evidently attained when $C_4$–$C_6$ diols are employed. The decreasing activity when using higher glycols, however, still ensures sufficient reaction rates.

The transesterification products obtained with dicarboxylic acid alkyl esters are especially suitable for the production of polyesters. Polyesters with only insignificant discolouration are obtained, as the catalysts employed have a stabilising action on the reaction melt, even in the presence of a polycondensation catalyst. In particular, titanium, tin or antimony compounds are employed as polycondensation catalysts.

The invention is illustrated in more detail by the following Examples. The intrinsic viscosity is determined in solutions of 1 g of polyester in 100 ml of a mixture consisting of equal parts of phenol and symmetrical tetrachloroethane at 30° C.

EXAMPLE 1 TO 8 AND COMPARISON EXAMPLE

A glass reactor (200 ml) with nitrogen inlet, descending cooler and condenser filled with methanol acting as dephlegmator is charged with dimethyl terephthalate and a glycol in the molar ratio 1:2. Then the catalyst is added and the reactor is heated in an oil bath. The methanol formed (theoretical amount 8 ml) is collected and measured. The further conditions of the experiments with different diols, temperature, reaction time and catalyst are indicated in the following table.

| Example | Diol | Catalyst [1% by weight] | Reaction time [h] | Reaction temperature [°C.] | Amount of distillate [ml] |
|---|---|---|---|---|---|
| Comparison | ethylene glycol | benzenephosphonic acid | 2 h | 260 | — |
| 1 | propanediol-1,3 | benzenephosphonic acid | 2h, 10min | 250 | 2.8 |
| 2 | butanediol-1,4 | benzenephosphonic acid | 3 h | 250 | 10* |
| 3 | hexanediol-1,6 | benzenephosphonic acid | 2h, 30min | 260 | 7.5 |
| 4 | decanediol-1,10 | benzenephosphonic acid | 2h, 40min | 260 | 5.6 |
| Comparison | ethylene glycol | methylphosphonic acid | 2 h | 250 | — |
| 5 | propanediol-1,3 | methylphosphonic acid | 4 h | 250 | 2.2 |
| 6 | butanediol-1,4 | methylphosphonic acid | 2h, 35min | 250 | 9* |
| 7 | hexanediol-1,6 | methylphosphonic acid | 3h, 45min | 250 | 7.6 |
| 8 | decanediol-1,10 | methylphosphonic acid | 3h, 15min | 250 | 5 |

*distillate contains about 35% of tetrahydrofurane

USE EXAMPLE

2% by weight of $Sb_2O_3$ are added to a transesterification mixture obtained as in Example 2. Then a vacuum of 0.3 torr is applied at 250° C. in the course of 1 hour. The polycondensation is complete after a further 2 hours and 20 minutes. The product is a white poly-1,4-butyleneterephthalate with an intrinsic viscosity of 0.80 dl/g.

COMPARISON EXAMPLE 1

Using 1% by weight of toluenesulfonic acid as catalyst, a transesterification product is prepared as in Example 2. The transesterification distillate contains about 40% of methanol, and the remainder is tetrahydrofuran. A subsequent polycondensation according to the procedure of the use example yields only an oligomer mixture with a relative viscosity of less than 1.10 and a Yellowness Index of 17.0.

COMPARISON EXAMPLE 2

The procedure of Comparison Example 1 is repeated, using 1% by weight of phosphoric acid as transesterification catalyst. The distillate likewise contains about 40% of methanol and tetrahydrofurane as remainder. The subsequent polycondensation results in a oligomer product with a relative viscosity of about 1.10 and a Yellowness Index of 10.7.

What is claimed is:

1. An improved process for the transesterification of an alkyl ester of a mono- or polycarboxylic acid with an aliphatic or cycloaliphatic diol containing at least 3 carbon atoms, in the presence of an acid catalyst, in a temperature range between 180° and 280° C., wherein the improvement comprises carrying out the transesterification in the presence of a catalytically effective amount of one or more phosphonic acid of the formula $$RP(O)(OH)_2$$

wherein R is alkyl of 1 to 20 carbon atoms or cycloalkyl of 5 to 6 carbon atoms.

2. A process according to claim 1, wherein the phosphonic acid is added in amounts of 0.1 to 5% by weight based on the reactants.

3. A process according to claim 1, wherein R is alkyl of 1 to 10 carbon atoms or cyclohexyl.

4. A process according to claim 1, wherein the transesterification is carried out in the temperature range between 200° and 260° C.

5. A process according to claim 1, which comprises the use of alkyl esters of mono-, di- or tricarboxylic acids.

6. A process according to claim 1, wherein the alkyl esters contain 1 to 10 carbon atoms in the alkoxy moiety.

7. A process according to claim 1, wherein the diol contains 3 to 10 carbon atoms.

8. A process according to claim 1, which comprises the use of alkyl esters of aliphatic, cycloaliphatic or aromatic dicarboxylic acids or mixtures thereof.

9. A process according to claim 2 wherein the phosphonic acid is added in amounts of 0.5 to 2% by weight based on the reactants.

10. A process according to claim 1 wherein R contains 1 to 10 carbon atoms.

11. A process according to claim 3 wherein R is alkyl of 1 to 4 carbon atoms.

12. A process according to claim 1 wherein the alkyl esters contain 1 to 4 carbon atoms in the alkoxy moiety.

* * * * *